US011246650B2

(12) United States Patent
Germain et al.

(10) Patent No.: US 11,246,650 B2
(45) Date of Patent: Feb. 15, 2022

(54) ARTHROSCOPIC DEVICES AND METHODS

(71) Applicant: RELIGN Corporation, Campbell, CA (US)

(72) Inventors: Aaron Germain, San Jose, CA (US); Jeff Norton, Emerald Hills, CA (US)

(73) Assignee: Relign Corporation, Campbell, CA (US)

( * ) Notice: Subject to any disclaimer, the term of this patent is extended or adjusted under 35 U.S.C. 154(b) by 42 days.

(21) Appl. No.: 16/738,805

(22) Filed: Jan. 9, 2020

(65) Prior Publication Data

US 2020/0222108 A1 Jul. 16, 2020

Related U.S. Application Data

(60) Provisional application No. 62/790,780, filed on Jan. 10, 2019.

(51) Int. Cl.
| | | |
|---|---|---|
| *A61B 18/14* | (2006.01) | |
| *A61B 18/04* | (2006.01) | |
| *A61B 17/00* | (2006.01) | |
| *A61B 18/00* | (2006.01) | |
| *A61B 17/32* | (2006.01) | |
| *A61B 18/12* | (2006.01) | |

(52) U.S. Cl.
CPC ......... *A61B 18/148* (2013.01); *A61B 18/042* (2013.01); *A61B 17/320016* (2013.01); *A61B 2017/0088* (2013.01); *A61B 2018/00077* (2013.01); *A61B 2018/00184* (2013.01); *A61B 2018/00583* (2013.01); *A61B 2018/00589* (2013.01); *A61B 2018/126* (2013.01)

(58) Field of Classification Search
CPC ............... A61B 18/148; A61B 18/042; A61B 17/320016; A61B 2017/0088; A61B 2018/00077; A61B 2018/00184; A61B 2018/00583; A61B 2018/00589; A61B 2018/126
See application file for complete search history.

(56) References Cited

U.S. PATENT DOCUMENTS

| | | |
|---|---|---|
| 5,364,395 A | 11/1994 | West, Jr. |
| 5,904,681 A | 5/1999 | West, Jr. |
| 6,610,059 B1 | 8/2003 | West, Jr. |

(Continued)

FOREIGN PATENT DOCUMENTS

WO WO-2020146750 A1 7/2020

OTHER PUBLICATIONS

International search report with written opinion dated Mar. 10, 2020 for PCT/US2020/013115.

*Primary Examiner* — Tigist S Demie
(74) *Attorney, Agent, or Firm* — Schwegman Lundberg & Woessner, P.A.

(57) ABSTRACT

An arthroscopic tissue resecting probe includes an elongated shaft having outer and inner sleeves which are formed from an electrically conductive material extending about an axis to a working end. Outer and inner resecting windows are formed in the sleeves in the working end. The working end includes a ceramic body having a collar portion extending fully around a region of the outer sleeve proximal to outer resecting window. A radiofrequency (RF) electrode is disposed on an outer surface of the ceramic body and is spaced-apart from the outer resecting window.

20 Claims, 9 Drawing Sheets

(56) References Cited

U.S. PATENT DOCUMENTS

| | | | |
|---|---|---|---|
| 7,699,846 B2 | 4/2010 | Ryan | |
| 9,855,675 B1 | 1/2018 | Germain et al. | |
| 10,052,149 B2 | 8/2018 | Germain et al. | |
| 10,595,889 B2 | 3/2020 | Germain et al. | |
| 2013/0079769 A1* | 3/2013 | Humble | A61B 18/1482 606/41 |
| 2014/0088592 A1 | 3/2014 | Van Wyk et al. | |
| 2014/0100567 A1* | 4/2014 | Edwards | A61B 18/148 606/42 |
| 2017/0202612 A1* | 7/2017 | Germain | A61B 18/1482 |
| 2017/0224368 A1 | 8/2017 | Germain et al. | |
| 2017/0252099 A1* | 9/2017 | Orczy-Timko | A61B 18/1206 |
| 2017/0258519 A1 | 9/2017 | Germain et al. | |
| 2017/0303990 A1 | 10/2017 | Benamou et al. | |
| 2018/0147003 A1 | 5/2018 | Shadduck et al. | |

\* cited by examiner

ARTHROSCOPIC DEVICES AND METHODS

CROSS-REFERENCE TO RELATED APPLICATIONS

This application claims the benefit of U.S. Provisional No. 62/790,780, filed Jan. 10, 2019, the entire content of which is incorporated herein.

BACKGROUND OF THE INVENTION

1. Field of the Invention

This invention relates to a medical system that includes variations of motor-driven arthroscopic shavers that carry RF electrodes for ablating or coagulating tissue.

2. Description of the Background Art

In arthroscopic procedures including subacromial decompression, anterior cruciate ligament reconstruction involving notchplasty, arthroscopic resection of the acromioclavicular joint and other similar procedures, there is a need for cutting, removal and/or contouring of soft tissue. Currently, surgeons use arthroscopic shavers and burrs having rotational cutting surfaces to remove soft tissue and bone in such procedures. Additionally, surgeons use electrosurgical ablation devices for ablating, coagulating or contouring soft tissue.

To promote efficiency, arthroscopic tool systems for mechanical cutting of soft tissue include a reusable motor-drive handpiece and interchangeable probes or shaver blades having different working ends for use in different aspects of a procedure. Typically, the electrosurgical devices consist of separate hand-held probes that are used independently of the motor-drive handpiece. Thus, in a typical arthroscopic procedure, the physician must exchange the tools frequently which is inefficient and potentially could increase the chances of introducing infectious agents into the working space.

A number of arthroscopic shavers and devices have been proposed in the prior art that combine a mechanical cutting tool, such as a shaver blade or burr, with electrosurgical components capable of coagulating or ablating tissue. Such cutting tools also include an integrated aspiration mechanism for extracting resected tissue, irrigation fluid and ablation debris. For example, arthroscopic probes with an elongated shaft with a working end that carries a motor-driven rotating mechanical cutting member and an RF electrode arrangement include the following examples: U.S. Pat. No. 5,364,395 to West ("West '395") and U.S. Pat. No. 5,904,681 to West ("West '681"), U.S. Pat. No. 6,610,059 to West ("West '059") and U.S. Pat. No. 7,699,846 to Ryan ("Ryan '846").

The West cases (West '395, West '059 and West '681) describe similar conventional arthroscopic shavers and burrs with a stationary windowed outer sleeve and a rotating inner cutting member. An RF electrode is carried at the working end of the outer sleeve opposing the window and rotating cutting member. Thus, the working ends of the probes in the West cases (West '395, West '059 and West '681) are adapted for tissue cutting or burring on one side of the probe and delivering RF ablation or coagulation energy on the opposing side of the working end. In typical probes, the interior of the rotating inner sleeve has a bore that communicates with an aspiration source for extracting tissue debris and fluid from the working space. In a typical variation in the West cases, an ablation electrode is carried on an insulated base member that is affixed to a metal outer sleeve.

There are several problems with the designs of devices disclosed in the West cases. First, as shown in FIG. 2, (which is combined FIGS. 16-17 of West '395), the electrode is projecting significantly outwardly from the outer diameter OD of the outer sleeve. Such a probe design would not be suitable for maneuvering in tight spaces between bone surfaces in a joint. Further it would be questionable whether such an electrode could be attached securely to an outer sleeve without being in danger of detaching during use as surgeons often apply substantial forces on the probe working end, for example, using the shaft as a lever. Further, in FIG. 2, it can be seen that the total insertion profile AA is large compared to the diameter of the tissue extraction channel BB. In a device described in West '681 as shown in FIG. 3, the electrode variation shown still extends outwardly from the outer diameter OD the outer sleeve which is disadvantageous. Also in West '681 (FIG. 3), the insulator base with the electrode is very small with no disclosure on how it can be reliably affixed to the outer sleeve without danger of breakage.

Still further in West '681(FIG. 3), the RF electrode comprises a number of wire-like projecting elements that would have a short operating life if manufactured as shown. In a device described in West '059 shown in FIG. 4, a similar RF electrode is disclosed with the improvement being an aspiration port near the electrode which would be less than optimal. During use, a vapor pocket is formed around the RF electrode which can obscure endoscopic vision. To remove the vapor pocket and bubbles, an aspiration port can be provided under or near the RF electrode, but it is unclear whether the location of the aspiration port as shown in West '059 would be effective. Again, in both West '681 (FIG. 3) and West '059 (FIG. 4), it can be seen in the schematic views that the diameter of the fluid extraction channel BB is small relative to the insertion profile AA of the working end.

In the device described in Ryan '846 case shown in FIG. 5, the shaft assembly includes three concentric sleeves which form the mechanical cutting mechanism as well as an active RF electrode sleeve. While this design allows for an electrode that does not project outwardly from the surface of the outer sleeve as in the West cases, this Ryan '486 case again results in the fluid extraction channel having diameter BB that is small relative to the outer diameter or insertion profile AA of the shaft which is a disadvantage. A further disadvantage of the Ryan '846 case is that the distal edge of the cutting sleeve is spaced very far inwardly from the distal tip of the outer sleeve, indicated at CC, due to the triple sleeve assembly.

Although the West cases were filed between 1993 and 2002, in other similar cases have been filed in a similar timeframe, there still has been no combination arthroscopic shaver/RF devices that have the desire functionality to displace the use of separate shaver blades and RF probes. In current practices in arthroscopy, physicians in virtually all cases use a mechanical shaver or burr for cutting soft tissue and bone, and then use a separate RF probe for ablating or coagulating tissue.

In view of the foregoing, it can be understood that that improved mechanical/electrosurgical probes are needed in arthroscopy. From the outline above, it can be understood that such a combination mechanical/RF shaver will be commercially useful only if such a shaver has the following features and operating functionality:

First, in order to be used in most arthroscopic procedures such as shoulders and knees, the probe must have a small outer shaft diameter or insertion profile, for example, less than 6.5 mm, or more often less than 5.5 mm, which is well known in the field of arthroscopy.

Second, the disposable shaver/RF probe must be adapted to function with a conventional motor-drive handpiece for rotating an inner sleeve relative to an outer sleeve in an elongated shaft. Further, a bore in the inner sleeve must communicate with a negative pressure source for extracting fluid and resected tissue from a working space. In this regard, the shaft components must allow for a relatively large diameter extraction channel that allows for up to 400 ml/min flows. It has been found that a 3.3 mm diameter extraction channel may provide suitable functionality in a 5.5 mm device, with 3.5 to 4.5 mm extraction channels being preferable. Stated another way, in a preferred variation, the ratio of the extraction channel diameter to the maximum insertion profile diameter should be at least 0.6:1.

Third, in a typical arthroscopic procedure in a patient's shoulder, it is often necessary for the physician to apply substantial force on the working end of the probe and therefore the electrode arrangement must be extremely durable without portions of the electrode assembly projecting outwardly from the insertion profile. Otherwise, the electrode arrangement can break when the working end is being torqued between bones in a working space.

Fourth, the electrode arrangement on the working end of an arthroscopic probe must be designed to operate for 10 or 15 minutes. That is, the electrode arrangement must be long-lasting as well as the physically durable. As is known, plasma formation around the electrode surface will erode the electrode over time so that the electrode surface area has to be sufficiently large to accommodate slight erosion over time while still functioning effectively.

Fifth, the working end of probe must be configured with fluid outflow channels in or around the electrode that optimize plasma ignition as well as for allowing aspiration of bubbles around the electrode to allow better visualization in an arthroscopic procedure.

Sixth, a combination mechanical/RF probe should be similar to conventional mechanical shavers wherein the cutting window of the inner rotating sleeve is very close to the distal tip of the outer sleeve so as to allow for tissue cutting when the distal tip is pressed against tissue. In other words, in electrode arrangement and insulator should not extend an excessive distance distally from the cutter window.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to arthroscopic shavers, tissue cutting devices and related methods of use. Several variations of the invention will now be described to provide an overall understanding of the principles of the form, function and methods of use of the devices disclosed herein. In general, the present disclosure provides for variations of arthroscopic tools adapted for cutting soft tissue and for RF ablation and/or coagulation. The arthroscopic tools are typically disposable and are configured for detachable coupling to a non-disposable handpiece that carries a motor drive component. This description of the general principles of this invention is not meant to limit the inventive concepts in the appended claims.

Figure 1:
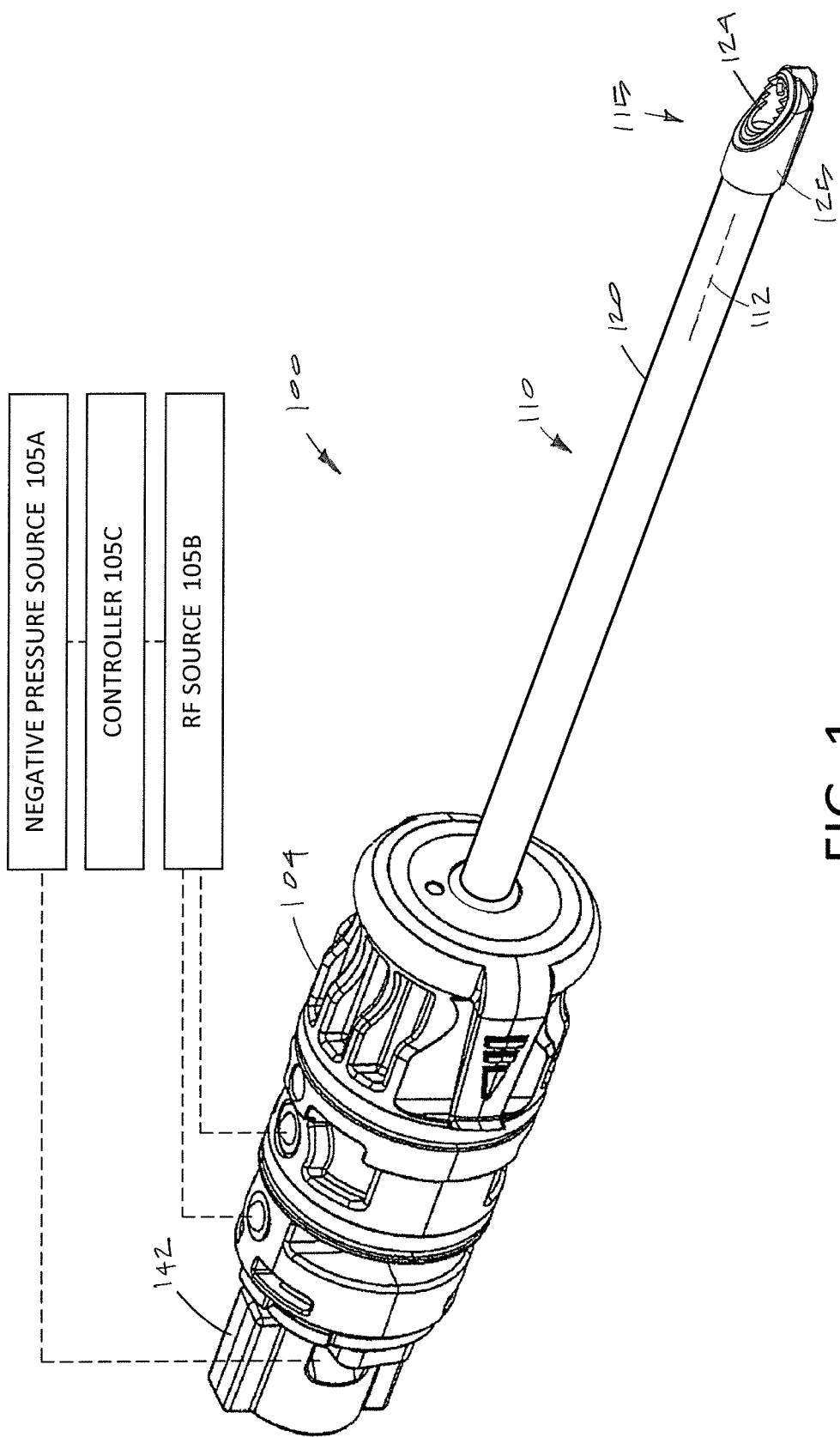
FIG. 1 is a perspective view of a disposable arthroscopic cutting probe that is adapted for detachable coupling to a motor drive handpiece were in the working end includes a rotating shaver blade in the ceramic housing carried an active electrode.
Figure 2:
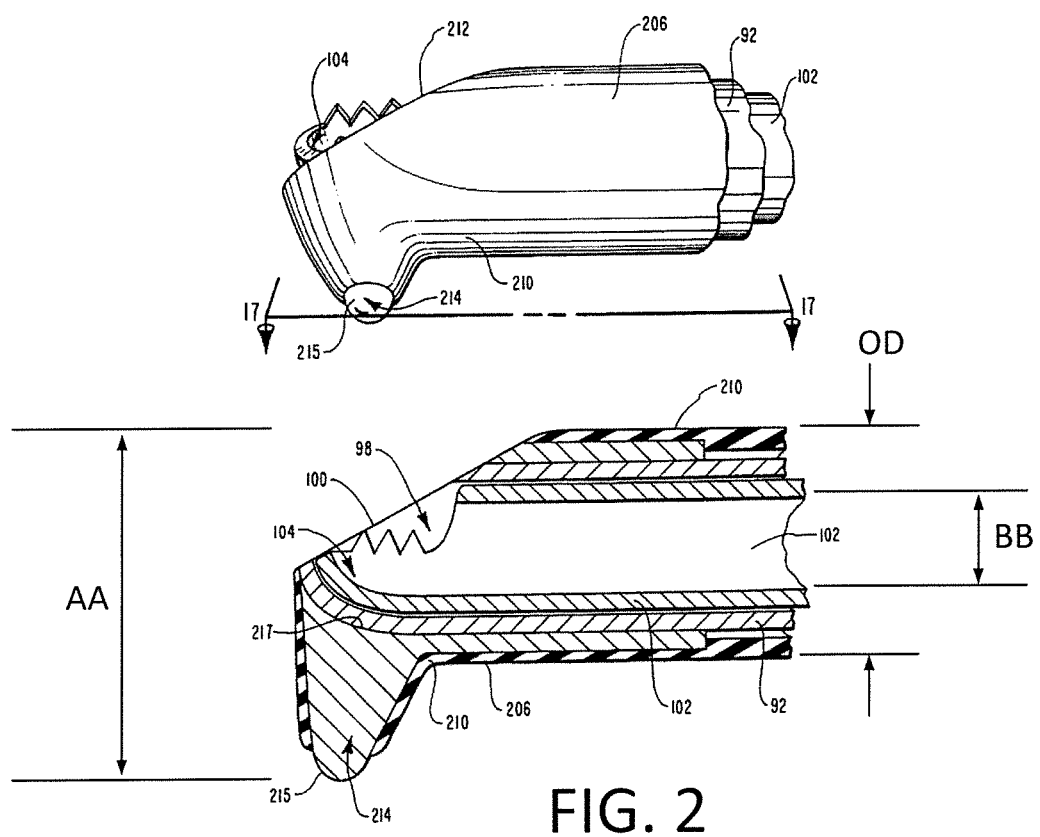
FIG. 2 is a prior art working end of a rotating cutter that carries an electrode arrangement as in U.S. Pat. No. 5,364,395 to West.
Figure 3:
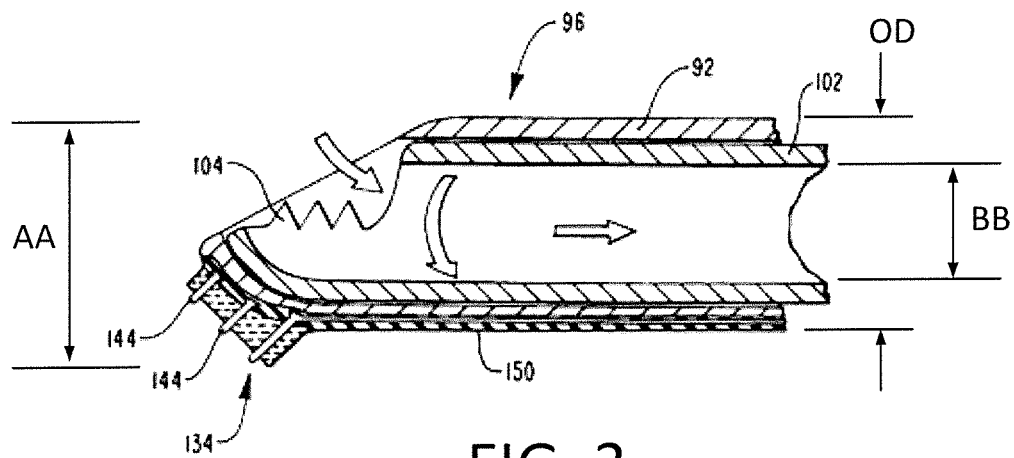
FIG. 3 is another prior art working end of a rotating cutter that carries an electrode arrangement as in U.S. Pat. No. 5,904,681 to West.
Figure 4:
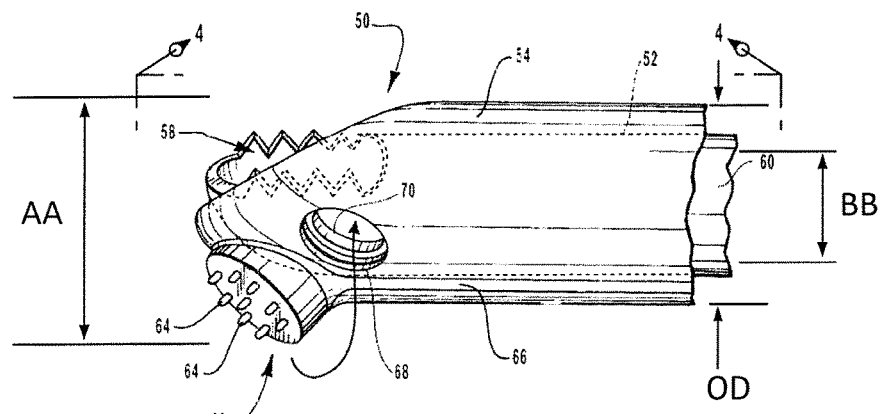
FIG. 4 is yet another prior art working end of a rotating cutter that carries an electrode arrangement as in U.S. Pat. No. 6,610,059 to West.
Figure 5:
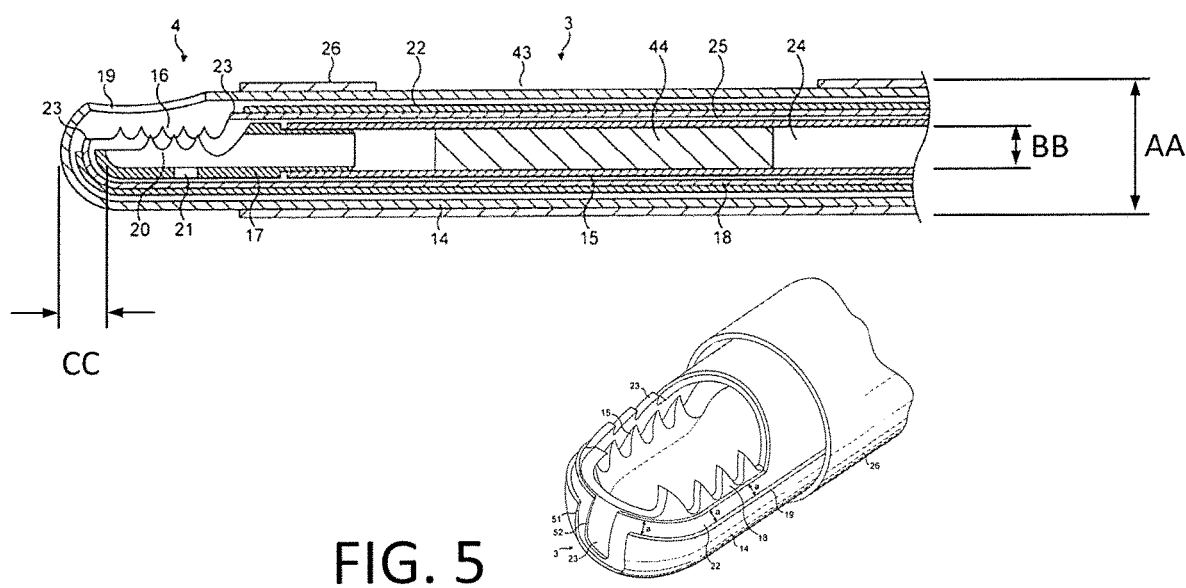
FIG. 5 another prior art working end of a rotating cutter that carries an electrode arrangement as in U.S. Pat. No. 7,699,846 to Ryan.
Figure 6A:
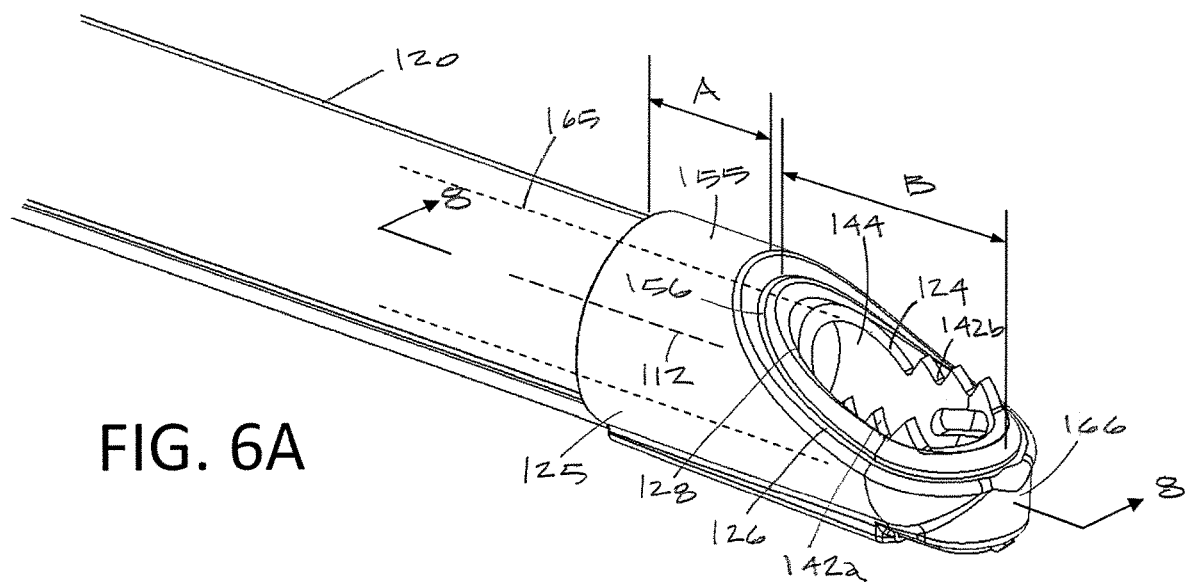
FIG. 6A is an enlarged perspective view of the working end of the probe of FIG. 1 showing the ceramic housing coupled to the outer sleeve and a rotating inner cutter when the electrode is hidden from view the opposing side of the ceramic housing.
Figure 6B:
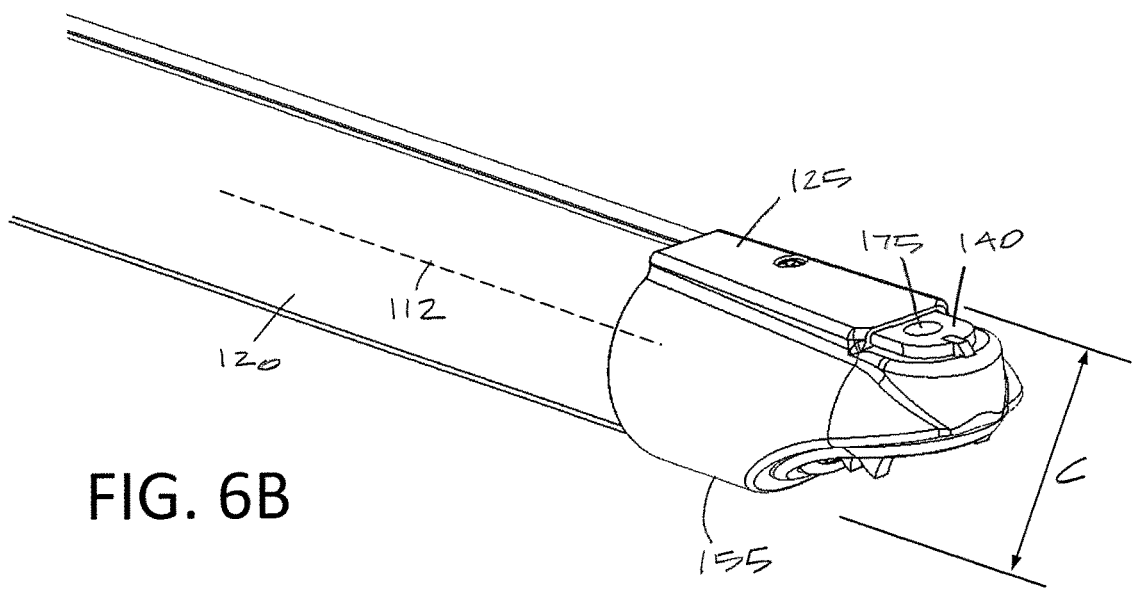
FIG. 6B is an enlarged perspective view of the working end FIG. 6A rotated 180° to show the electrode carried by the ceramic housing.

In one variation shown in FIGS. 1, 6A and 6B, a disposable shaver or probe 100 of the invention has a proximal hub 104 (FIG. 1) that can be received by a receiver or bore in an arthroscopic handpiece that carries a motor drive. Such motor drive handpieces may be further described in the following co-pending and commonly owned patent applications: Ser. No. 15/271,184 filed Sep. 20, 2016 titled ARTHROSCOPIC DEVICES AND METHODS; Ser. No. 15/410,723 filed Jan. 19, 2017 titled ARTHROSCOPIC DEVICES AND METHODS; Ser. No. 15/454,342 filed Mar. 9, 2017 titled ARTHROSCOPIC DEVICES AND METHODS; and Ser. No. 15/483,940 filed Apr. 10, 2017 titled ARTHROSCOPIC DEVICES AND METHODS.

In one aspect, the probe 100 has a working end 115 that carries a high-speed rotating cutter that is configured for mechanical tissue cutting in many arthroscopic surgical applications, including but not limited to cutting tissue in shoulders, knees, hips, wrists, ankles and the spine. Further, the probe includes a bi-polar electrode arrangement for ablating tissue with plasma in a saline environment as is known in the art. Referring to FIG. 1, the hub 104 of the probe 100 is adapted for coupling to a negative pressure source 105A, an RF source 105B and a controller 105C as also described in the above co-pending patent applications.

In FIGS. 1 and 6A, it can be seen that probe 100 has a shaft or shaft assembly 110 extending along longitudinal axis 112 to the working end 115. The shaft assembly 110 comprises a typically metal outer sleeve 120 and an inner sleeve 122 (FIG. 8) rotatably disposed therein. The inner sleeve 122 has a distal cutting portion or member 124. The outer sleeve 120 carries a distal dielectric body or housing 125 (typically called ceramic housing 125 herein) with a window 126 therein that surrounds an outer window 128 in the outer sleeve 120. An electrode 140 is carried on the ceramic housing 125 on the side opposing the window 126 in the ceramic housing. It should be appreciated that the electrode can consist of a plurality of exposed electrode elements and may be disposed close to window 126 on one side or both sides. The electrode location, or plurality of electrode elements, may be asymmetrically disposed around the circumference of the ceramic housing relative to the window. The shaft assembly 110 extends from the proximal hub 104 wherein the outer sleeve 120 is coupled in a fixed manner to the hub 104 which can be an injection molded plastic, for example, with the outer sleeve 120 insert molded therein. The inner sleeve 122 is coupled drive coupling 142 (FIG. 1) that is configured for coupling to the rotating motor shaft of the motor drive handpiece.

More in particular, referring to FIG. 6A, the rotatable cutting member 124 is a metal cutter with sharp cutting edges 142a and 142b on opposing sides of inner window 144 in the cutting member 124 for cutting soft tissue. The motor drive is operatively coupled to the cutter to rotate the cutting member at speeds ranging from 1,000 rpm to 20,000 rpm.

Figure 8:
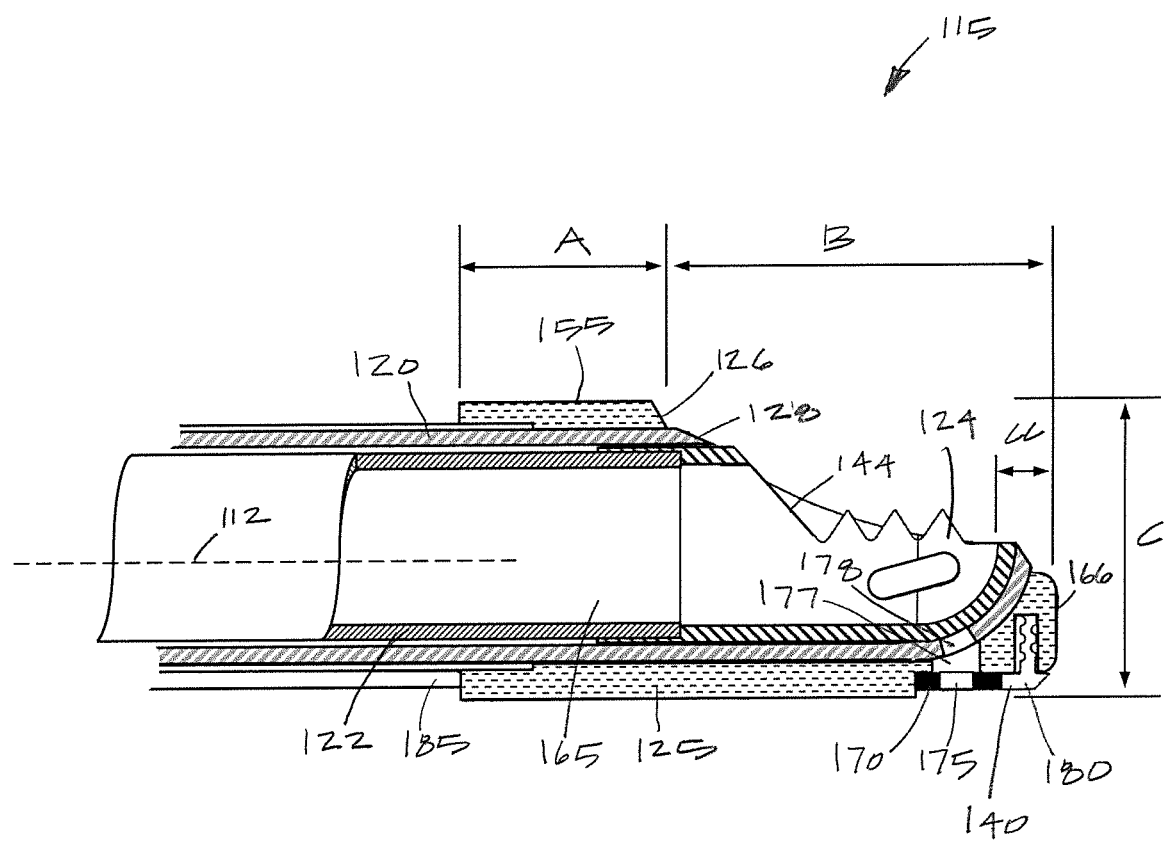
FIG. 8 is a sectional view of the working end of FIG. 6A taken along 8-8 of FIG. 6A showing the ceramic housing coupled to the outer sleeve, an active electrode carried the surface of the ceramic housing and a rotating inner cutter.

In one aspect of the invention referring to FIGS. 6A, 6B and 8, the ceramic housing 125 is adapted to be extremely strong and durable besides providing a dielectric base for carrying the electrode 140. As described above, the working end 115 may be used as a lever between bones in a joint and therefore the ceramic has to be extremely durable. Thus, one means of providing a durable ceramic housing 125 is to have a collar portion 155 of the ceramic housing 125 extending 360° around the outer sleeve 120. Further, the ceramic housing 125 and window 126 therein extends entirely around the window 128 in the outer sleeve 120 and can be secured to the outer sleeve 120 with adhesives or an otherwise very tight fit. For additional strength, the collar portion 155 as an axial length A that is long enough to strengthen the housing 125, wherein such axial length A can be at least 0.020" as further described below. Stated another way, the axial length A of the collar portion 155 of the ceramic housing 125 is at least 25% of the length B of the window 126 in the ceramic housing 125 (see FIG. 6A). More often, the axial length A of the collar 155 is at least 35% of the axial length B of the ceramic window 126.

In general, an arthroscopic probe of corresponding to invention consists of an elongated shaft comprising outer and inner sleeves, 120 and 122, of an electrically conductive material extending about an axis 112 to a working end 115, the sleeves configured with respective outer and inner resecting windows in the working end, a ceramic body 125 of the working end having a collar portion 155 extending in 360° around a region of the outer sleeve 120 proximal to the outer resecting window 128, and an RF electrode 140 disposed on an outer surface of the ceramic body spaced apart from the outer resecting window. In one variation, the collar portion 155 has an axial length of at least 0.020", at least 0.050", at least 0.100", at least 0.150" or at least 0.200".

Further, the arthroscopic probe 100 has a distal ceramic housing 125 with the collar portion 155 as described above wherein the wall thickness of the ceramic collar 155 surrounding the outer sleeve 120 is at least 0.005", at least 0.010" or at least 0.015". The thickness of the ceramic body 125 is at least 0.010", at least 0.012" or at least 0.020" around the interior bore carrying the inner sleeve 122.

Further, still referring to FIGS. 6A and 6B, the working end 115 has an insertion profile with a maximum cross-section dimension indicated at C in FIG. 6B of less than 6.5 mm and often less than 5.5 mm. In one variation, the ceramic housing 125 is fabricated from a ceramic selected from the group of Alumina, Zirconia, an Alumina-Zirconia composite, Silicon Nitride, Silicon Carbide, synthetic Ruby and synthetic Sapphire.

In another aspect of the invention, the ceramic body 125 is fabricated such that the window 126 therein has small radiuses or chamfers 156 in the window edges (FIG. 6A) so that such ceramic window edges are set back from the metal edges of window 128 in outer sleeve 120 by a small dimension, for example, between 0.005" and 0.010". Thus, the assembly of the outer sleeve 120 and the closely fitting ceramic housing 125 are configured to be strong and durable.

In another aspect of the invention, the bore or passageway 165 in inner sleeve 122 that communicates with negative pressure source 105A is relatively large relative to the insertion profile C of the working end 115 (see FIGS. 6A-6B and 8). In one variation, the ratio of the cross-section of the bore 165 relative to the insertion profile cross-section C is at least 0.5:1, at least 0.6:1 or at least 0.7:1. As can be seen in FIG. 8, a further advantage of the working end is that the distal edge of the cutting member 124 is spaced close to the distal tip 166 of probe indicated at CC in FIG. 8, for example less than 0.15".

Figure 6C:
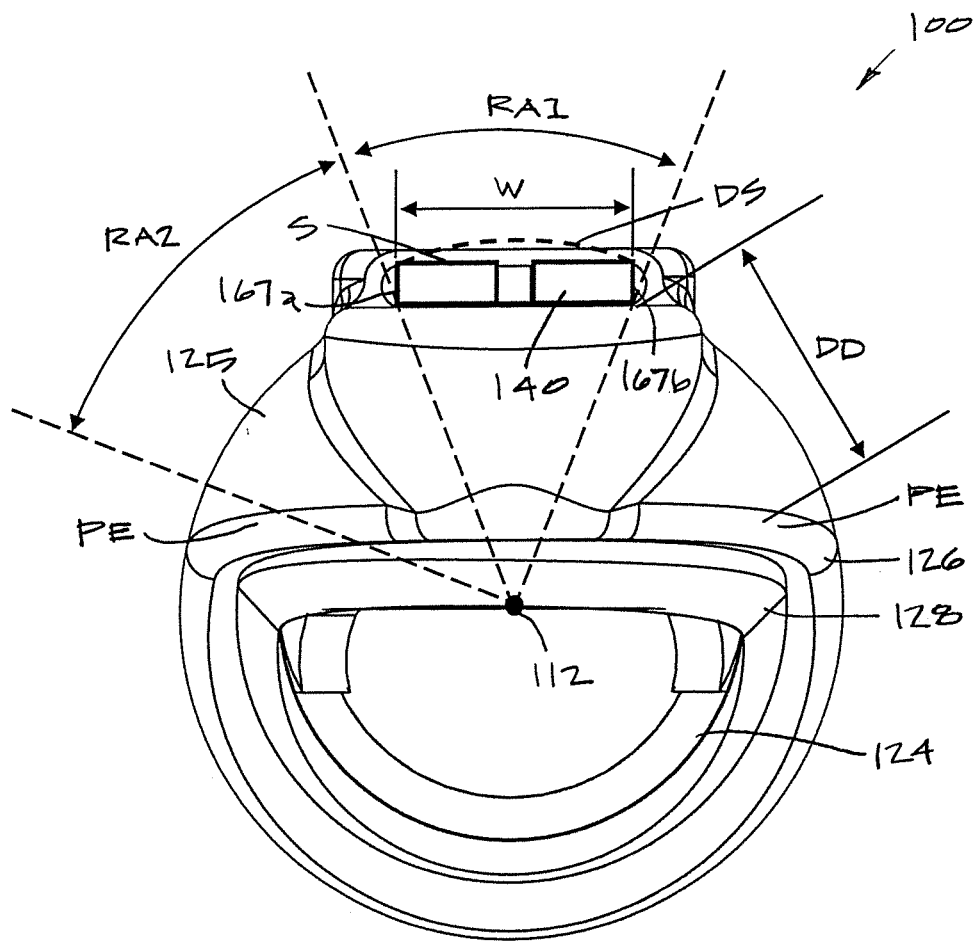
FIG. 6C is an end view of the working end of FIGS. 6A-6B showing dimensions of the electrode and spacing between lateral edges of the electrode and edges of the window in the outer sleeve.

FIG. 6C is an end view of probe 100 and illustrates aspects and dimensional characteristics of the electrode 140. In one aspect, the electrode 140 has a flat surface S that extends axially and is generally parallel to the axis 112 of the probe. In another variation indicated in phantom view in FIG. 6C, the electrode 140 can have a dome surface DS that extends axially and again is generally parallel to axis 112 of the probe.

FIG. 6C further illustrates the width WW of the electrode 140 which is typically at least 0.05" or at least 0.08" between lateral edges 167a and 167b thereof. Stated another way, the electrode 140 typically has a width WW having a radial angle RA1 of at least 15° when measured transverse to the axis 112. Often, the radial angle RA1 is at least 25°. Still referring to FIG. 6C, the edges 167a and 167b of electrode 140 are spaced apart from the closest or proximate edges PE of the window 126 in the ceramic housing 125 by a radial angle RA2 of at least 10° and often at least 20°. Stated another way, the edges 167a and 167b of electrode 140 are spaced apart from the closest or proximate edges PE of window 126 by distance DD which is at least 0.010" or at least 0.015". While the features and dimensions of the electrode 140 relative to the ceramic body 125 and a window is illustrated in an outer sleeve, similar features and dimensions can be provided in a rotating inner sleeve that carries a ceramic body and electrode.

Figure 7A:
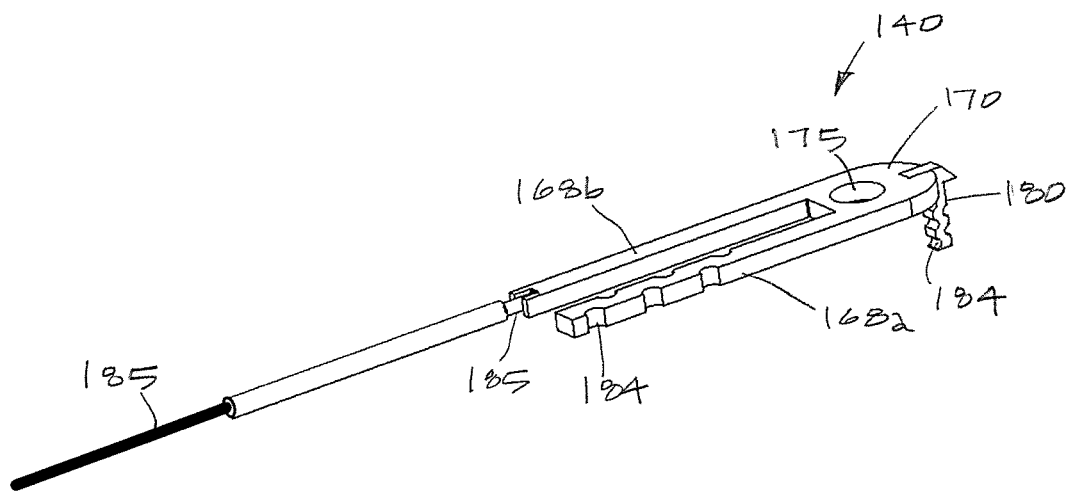
FIG. 7A is a perspective view of the active electrode of FIG. 6B shown removed from the ceramic housing.
Figure 7B:
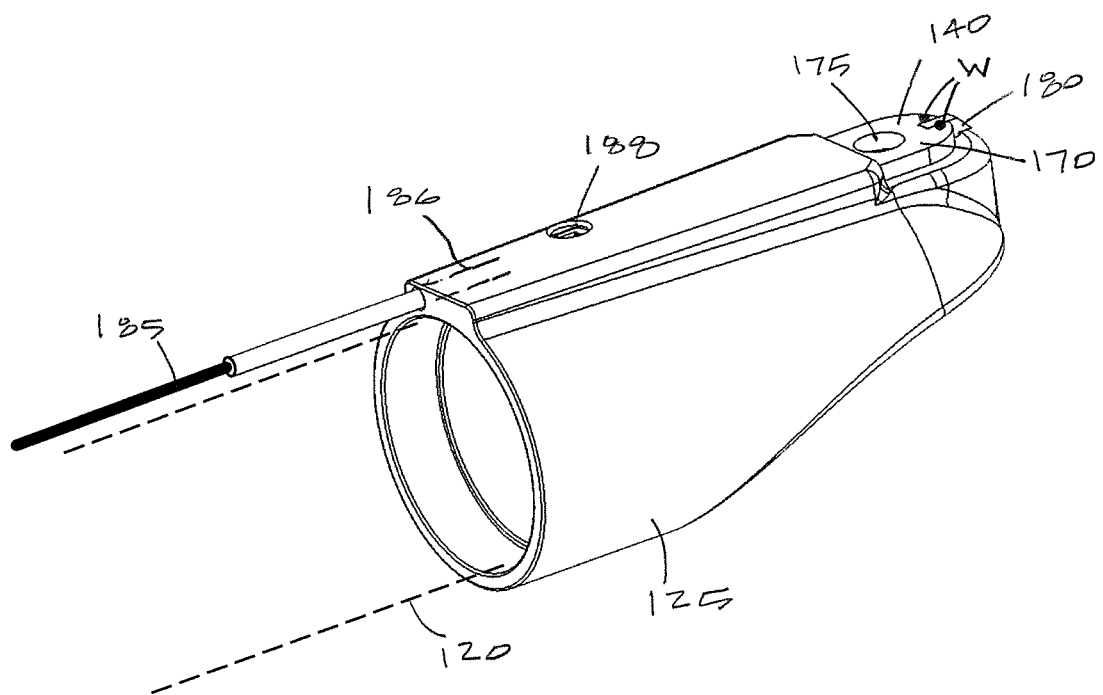
FIG. 7B is a perspective view of the working end of FIG. 6B showing the assembly of the ceramic housing and active electrode with the outer sleeve in phantom view.

Now turning to FIGS. 7A and 7B, in another aspect of the invention, the probe includes means for securing electrode 140 to the ceramic housing 125. As described previously, very durable connections are required between the electrode 140 and the ceramic housing 125. FIG. 7A shows electrode 140 separated from the ceramic housing 125 wherein the electrode has first and second anchor portions or legs 168a and 168b that are adapted for insertion into axially-extending bores or slots in the ceramic housing 125 (not visible). Further, an exposed portion 170 of electrode 140 includes an aperture 175 that communicates with an aperture 177 in the ceramic body which in turn communicates with aperture 178 in the outer sleeve 120 (see FIG. 8).

A separate metal pin 180 for securing the electrode is provided for insertion into a receiving bore 182 in the ceramic body 125 as can be seen in FIG. 8. Thus, in FIG. 7B, it can be understood that the electrode legs 168a and 168b can be inserted through receiving channels in the ceramic body 125 and can be further glued in place with notches 184 in a leg (and metal pin 180) adapted for holding an adhesive. The metal pin 180 can be inserted into bore 182 and then welded to the electrode 140 (see welds W in FIG. 6B) to secure the electrode in the ceramic housing 125.

Still referring to FIGS. 7A-7B, an electrical lead 185 then can be inserted through channel 186 in the ceramic body 125 to connect with electrode leg 186b. An opening 188 in the ceramic body 125 is provided to weld or solder the electrical lead 185 to electrode leg 186b. Thereafter, a potting material can be used to fill in the opening 188 to cover the electrical connection. In one aspect of the invention, the anchor shaft or leg portions 186a, 186b of the electrode 140 have a mean cross sectional dimension or thickness of at least 0.003" wherein such minimum dimensions are provided to prevent rapid erosion and burnout of the electrode. The exposed surface area of the electrode 140 is at least 0.009 in$^2$.

Figure 9:
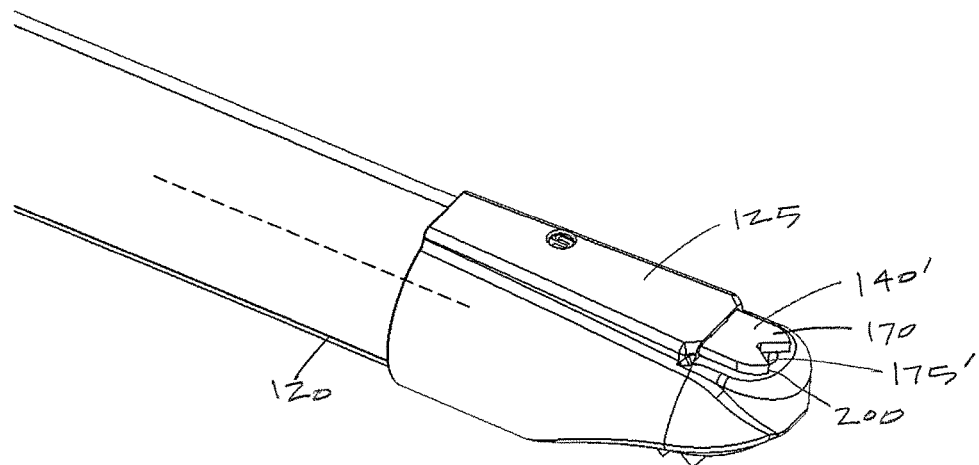
FIG. 9 is a perspective view of another working end similar to that of FIGS. 6A-6B with an active electrode that is cantilevered from slots in the ceramic housing.
Figure 10:
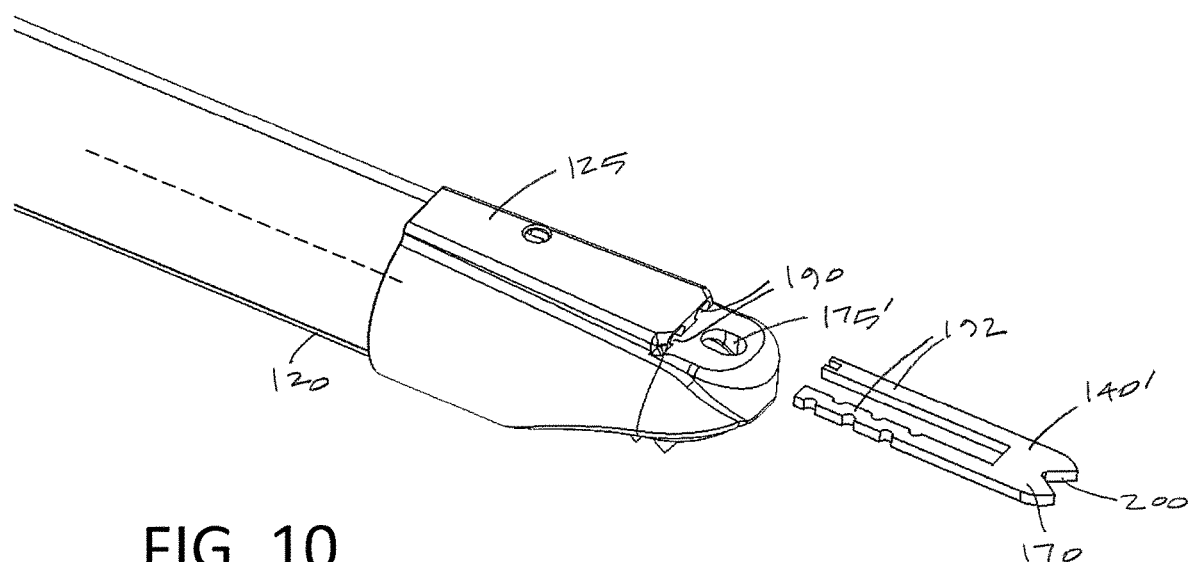
FIG. 10 is a perspective view of the working end of FIG. 9 in an explode view with the active electrode separated from the ceramic housing.

FIGS. 9 and 10 illustrate another embodiment of the working end 115 wherein the ceramic housing 125 has an electrode 140' that is adapted to cantilever from slots 190 in the ceramic housing 125. In this variation, the working end 115 does not require the additional metal pin 180 of FIG. 8 to secure the electrode to the ceramic housing 125 in a durable manner.

In general, an arthroscopic probe of the invention comprises an elongated shaft including outer and inner sleeves of an electrically conductive material extending about an axis to a working end of the shaft, the outer and sleeves configured with respective outer and inner resecting windows in the working end, a ceramic body carried by the outer sleeve at the working end, and an RF electrode disposed on the ceramic body wherein the RF electrode comprises an active surface portion and an anchor shaft portion disposed in an axial channel in the ceramic body configured to secure the RF electrode in the ceramic body. In one variation, the active surface portion of the electrode is cantilevered from the axial channel by at least 0.040" over a portion of the ceramic body. In a variation, the active surface portion of the electrode is cantilevered over an aperture in the ceramic body that communicates with a passageway in the shaft that is coupled to a negative pressure source.

Figure 11:
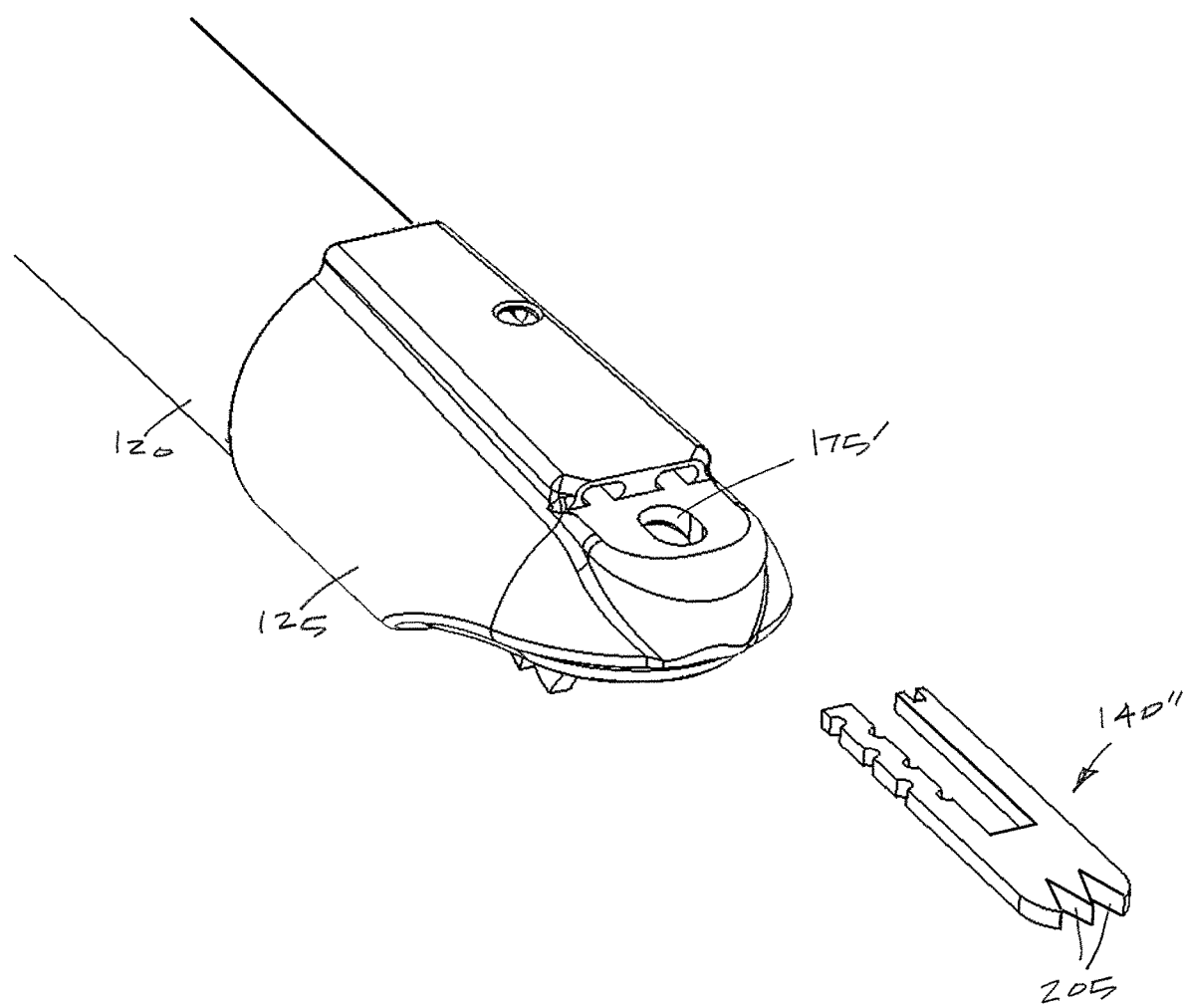
FIG. 11 is a perspective exploded view of another working end similar to that of FIG. 9 showing the active electrode separated from the ceramic housing.

In another aspect of the invention referring to FIGS. 10 and 11, the ceramic body 125 is configured with at least one slot 190 receiving an anchor portion 192 of an electrode 140' or 140" wherein the dimensions of the slot 190 are adapted to closely fit the dimensions of the electrode anchor portion 192 to thereby prevent plasma migration into the slot 190 which could the erode and burnout the electrode. In one variation, the gap dimension between the surface of the anchor portion 192 and the anchoring bore 190 is 0.005" or less, and more often 0.003" or less.

In general, an arthroscopic RF device of the invention for operating in a saline environment comprises an elongate sleeve extending about an axis to a distal dielectric body, an electrode carried by the dielectric body connected to an RF source having operating parameters for generating a tissue-ablating plasma around the electrode in the saline environment, wherein the electrode comprises an exposed surface portion and an anchor portion positioned in an anchoring bore in the dielectric body and wherein the cross section of the anchor portion is sufficiently tightly fitted in the cross section of the anchoring bore to prevent plasma formation around the anchor portion in the anchoring bore. Further, the portion of anchor portion 192 in the bore 190 with the tight gap dimension has a length of at least 0.020".

In another aspect of the invention, as can be seen in FIG. 10, the exposed surface portion 170 of the electrode 140 extends partly across the aperture 175' in the ceramic housing 125 wherein the electrode has a non-linear edge 200 extending across such aperture 175'. In one variation shown in FIG. 10, the electrode has a v-shaped edge extending over the aperture 175'. During use, the v-shaped edge 200 of the electrode 140 is adapted to ignite plasma faster due to a known "RF edge effect" and further the additional length of the two edges of the v-shape can erode more slowly during use than a shorter linear edge. During use, the erosion of electrode edge 200 then exposes a larger portion of the aperture 175' in the ceramic body 125. This is been found to be advantageous during use wherein the increasing exposure of aperture 175' in the ceramic housing 125 is adapted to the increase the efficiency of aspirating bubbles away from the energized electrode 140'. FIG. 11 shows a similar electrode 140" with a two v-shaped edges 205 that are adapted to extend across the aperture 175' in the ceramic body 125 for similar purposes.

In general, an arthroscopic RF device for operating in a saline environment comprises an elongate sleeve extending about an axis to a distal dielectric body, an electrode carried by the dielectric body connected to an RF source having operating parameters for generating a tissue-ablating plasma around the electrode in the saline environment, a rotatable member with a distal cutter rotatably disposed in sleeve, and an aperture in the dielectric body that communicates with a passageway in device coupled to a negative pressure source wherein the electrode prior to use has an exposed surface portion that extends partly across the aperture and thereby partly occludes the aperture. In one variation, the electrode prior to use occludes less than 80% of the aperture. In other variations, the electrode prior to use occludes less than 70% of the aperture, less than 60% of the aperture or less than 50% of the aperture. Further, the exposed surface portion of the electrode has a non-linear edge that extends partly across the aperture, which in one variation the electrode has a v-shape in the edge that extends partly across the aperture. In another variation, the electrode has a plurality of v-shapes in the edge that extends partly across the aperture.

In another variation, an arthroscopic device with the invention comprises an elongated shaft assembly have an insertion profile having a cross-sectional dimension, the shaft assembly comprising (i) an outer sleeve extending to a working end with a first window, (ii) an inner sleeve rotationally disposed in the outer sleeve with a second window communicating with a tissue extraction channel therein, and (iii) a ceramic body affixed to the outer sleeve and an electrode carried by the ceramic body wherein the electrode has a thickness of at least 0.003" and a surface area of at least 0.009 in$^2$ and wherein the electrode is spaced apart from the conductive outer sleeve by a ceramic body by at least 0.010". In this variation, the electrode comprises a surface portion and an anchor portion, wherein the anchor portion is disposed in an anchoring channel in the ceramic body per housing where the gap between surfaces of the anchor portion and anchoring channel is sufficiently small so as to choke plasma formation around said anchor portion.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic tissue resecting probe, comprising:
a hub;
an elongated shaft extending distally from the hub and comprising an outer sleeve and an inner sleeve which are each formed of an electrically conductive metal, the elongated shaft extending about a longitudinal axis to a working end of the elongated shaft that is located distally of the hub, wherein a proximal end of the outer sleeve is fixed to the hub, and wherein a proximal end of the inner sleeve is fixed to a drive coupling that is couplable to a motor shaft for rotating the inner sleeve within the outer sleeve and relative to the hub when the motor shaft is rotated;
an outer cutting window formed in a distal end of the outer sleeve;
an inner cutting window formed in a distal end of the inner sleeve;
wherein each of said outer cutting window and inner cutting window includes conductive metal cutting edges that can cut tissue when the inner sleeve is rotated within the outer sleeve;
a ceramic body including a ceramic window formed in a first side of the ceramic body, the ceramic body received on the distal end of the outer sleeve such that the ceramic window extends entirely around the outer cutting window in the distal end of the outer sleeve so as to expose entirely the outer cutting window through the ceramic window, wherein the ceramic body is fixed to the distal end of the outer sleeve so that the ceramic window remains fixed relative to the outer cutting window and thereby remains extending entirely around the outer cutting window when the inner sleeve is rotated within the outer sleeve; and
an electrode carried by the ceramic body on a second side of the ceramic body that is opposite the first side, wherein the electrode includes a proximal anchoring portion that is received in an anchoring slot in the second side of the ceramic body so as to leave a distal exposed portion of the electrode exposed along the second side of the ceramic body, wherein the second side of the ceramic body includes an aperture that communicates with an aperture in the outer sleeve, the distal exposed portion of the electrode extending partly across the aperture in the ceramic body to partly occlude the aperture in the ceramic body;
wherein a lateral edge of the distal exposed portion of the electrode is spaced-apart by a first radial angle of at least 10° from a closest lateral edge of the ceramic window in the ceramic body.

2. The arthroscopic tissue resecting probe of claim 1, wherein the first radial angle is at least 20°.

3. The arthroscopic tissue resecting probe of claim 1, wherein the lateral edge of the distal exposed portion of the electrode is spaced apart at least 0.010" from the closest lateral edge of the ceramic window in the ceramic body.

4. The arthroscopic tissue resecting probe of claim 1, wherein the distal exposed portion of the electrode occludes less than 70% of the aperture in the ceramic body.

5. The arthroscopic tissue resecting probe of claim 1, wherein the distal exposed portion of the electrode has a width of at least 0.05".

6. The arthroscopic tissue resecting probe of claim 1, wherein the distal exposed portion of the electrode has a width measured in a second radial angle of at least 15°.

7. The arthroscopic tissue resecting probe of claim 1, wherein the distal exposed portion of the electrode has a width measured in a second radial angle of at least 25°.

8. The arthroscopic tissue resecting probe of claim 1, wherein the elongated shaft has an insertion profile with a maximum cross-section of less than 6.5 mm.

9. The arthroscopic tissue resecting probe of claim 1, wherein the elongated shaft has an insertion profile with a maximum cross-section of less than 5.5 mm.

10. The arthroscopic tissue resecting probe of claim 1, wherein the distal exposed portion of the electrode includes a non-linear edge extending across the aperture in the ceramic body.

11. The arthroscopic tissue resecting probe of claim 1, wherein the ceramic body has a proximal collar portion extending 360° around the outer sleeve proximal to the outer cutting window.

12. The arthroscopic tissue resecting probe of claim 11, wherein said proximal collar portion has an axial length of at least 0.020".

13. The arthroscopic tissue resecting probe of claim 10, wherein the non-linear edge includes a v-shaped edge.

14. The arthroscopic tissue resecting probe of claim 11, wherein the proximal collar portion of the ceramic body has a wall thickness of at least 0.010".

15. The arthroscopic tissue resecting probe of claim 1, wherein the distal exposed portion of the electrode occludes less than 60% of the aperture in the ceramic body.

16. The arthroscopic tissue resecting probe of claim 1 further comprising a negative pressure source communicating with a passageway in the inner sleeve, wherein a ratio of a cross-section of said passageway relative to a maximum cross-section of an insertion profile of the elongated shaft is at least 0.5:1.

17. The arthroscopic tissue resecting probe of claim 1, wherein the proximal anchoring portion of the electrode comprises two legs.

18. The arthroscopic tissue resecting probe of claim 1, wherein the proximal anchoring portion of the electrode has a mean cross sectional dimension of at least 0.005".

19. The arthroscopic tissue resecting probe of claim 1, wherein the proximal anchoring portion of the electrode is configured with first and second anchor shaft portions disposed in respective first and second axial bores in the anchoring slot in the second side of the ceramic body.

20. The arthroscopic tissue resecting probe of claim 1, wherein the distal exposed portion of the electrode occludes less than 50% of the aperture in the ceramic body.

* * * * *